(12) United States Patent
Mizutani et al.

(10) Patent No.: US 6,740,217 B2
(45) Date of Patent: May 25, 2004

(54) STRUCTURE OF GAS SENSOR DESIGNED TO MINIMIZE ERROR OF SENSOR OUTPUT

(75) Inventors: Keigo Mizutani, Okazaki (JP); Eiichi Kurokawa, Okazaki (JP); Masahiro Taguchi, Nishio (JP); Daisuke Makino, Ichinomiya (JP)

(73) Assignees: Denso Corporation (JP); Nippon Soken Inc. (JP)

( * ) Notice: Subject to any disclaimer, the term of this patent is extended or adjusted under 35 U.S.C. 154(b) by 0 days.

(21) Appl. No.: 10/178,711

(22) Filed: Jun. 25, 2002

(65) Prior Publication Data

US 2002/0195338 A1 Dec. 26, 2002

(30) Foreign Application Priority Data

Jun. 25, 2001 (JP) ........................................ 2001-191472
Mar. 11, 2002 (JP) .......................................... 2002-65597

(51) Int. Cl.$^7$ ............................................ G01N 27/407
(52) U.S. Cl. ........................................ 204/426; 204/424
(58) Field of Search ................................. 204/421–429

(56) References Cited

U.S. PATENT DOCUMENTS 6,036,841 A * 3/2000 Kato et al. .................. 205/181

FOREIGN PATENT DOCUMENTS

| EP | 0 678 740 A1 | 10/1995 | ......... G01N/27/407 |
| JP | 2885336 | 2/1999 | .......... G01N/27/46 |

* cited by examiner

*Primary Examiner*—Alex Noguerola
(74) *Attorney, Agent, or Firm*—Nixon & Vanderhye PC

(57) ABSTRACT

A gas sensor consists of a pump cell, a monitor cell, and a sensor cell. The sensor cell is supplied with power to produce a sensor cell current. The monitor cell is supplied with power to produce a monitor cell current. A sensor cell and a monitor cell current detector are disposed between a sensor cell electrode exposed to a gas cavity and a sensor cell power supply and between a monitor cell electrode exposed to the gas cavity and a monitor cell power supply, thereby enabling the sensor cell current and the monitor cell current to be measured without addition of electric noises arising from current components flowing from the monitor cell to the sensor cell and vice versa.

4 Claims, 7 Drawing Sheets

Comparative Example

STRUCTURE OF GAS SENSOR DESIGNED TO MINIMIZE ERROR OF SENSOR OUTPUT

BACKGROUND OF THE INVENTION

1. Technical Field of the Invention

The present invention relates generally to a gas sensor which may be used to measure the concentration of a specified gas component such as a nitrogen oxide contained in exhaust gasses of an automotive engine, and more particularly to an improved structure of such a gas sensor element designed to minimize an error of a sensor output.

2. Background Art

NOx sensors which are installed in an exhaust system of an automotive engine and equipped with electrochemical cells called a monitor cell, a pump cell, and a sensor cell formed on solid electrolyte plates are typically used for burning control of the engine. The pump cell works to keep the concentration of oxygen ($O_2$) within a measurement gas chamber at approximately zero. The monitor cell outputs an electromotive force or limiting current as a function of the concentration of oxygen within the measurement gas chamber. The output of the monitor cell is fedback to the pump cell to pump the oxygen molecules inside or outside the measurement gas chamber. The sensor cell works to dissociate NOx molecules within the measurement gas chamber and discharge oxygen produced when the NOx molecules dissociated to produce a current as a function of the concentration of NOx molecules.

FIG. 7 shows a comparative example of a NOx sensor.

The illustrated structure has the monitor cell 3 disposed in the vicinity of the sensor cell 4, which may cause oxygen ion currents to flow, as indicated by an arrow a, from the measurement gas electrode 31 to the reference electrode 32 of the monitor cell 3 and, as indicated by an arrow d, from a measurement gas electrode 41 of the sensor cell 4 to the reference electrode 32 of the monitor cell 3.

The NOx sensor has a monitor circuit 93 equipped with a power supply 932 and a monitor cell current detector 931. The monitor current detector 931 measures an undesirable current arising from the oxygen ion currents a and d. Correctly, a current flow produced in the monitor cell 3 as a function of the concentration of oxygen is provided by the sum of a and c. A difficulty is, thus, encountered in the monitor cell 3 to measure the concentration of oxygen accurately.

Similarly, a current flow produced in the sensor cell 4 as a function of the concentration of NOx is provided by the sum of b and d, but however, a sensor circuit 94 equipped with a power supply 942 and a sensor cell current detector 931 measures an undesirable current arising from the sum of b and c. An error is, thus, added to an output of the sensor cell 4.

The above problem is encountered commonly in gas sensors of the type wherein the monitor cell and the sensor cell are both employed.

SUMMARY OF THE INVENTION

It is therefore a principal object of the present invention to avoid the disadvantages of the prior art.

It is another object of the present invention to provide a gas sensor which is designed to minimize an error of a senor output.

According to one aspect of the invention, there is provided a gas sensor which may be installed in an exhaust pipe of an internal combustion engine to measure the concentration of an oxygen-containing gas component which is dissociative to produce oxygen ions or an oxygen-active gas component which is reactive to oxygen ions such as NOx, CO, or HC contained in exhaust gasses for use in engine burning control and/or catalytic systems.

The gas sensor comprises: (a) a gas cavity into which gasses consisting essentially of oxygen molecules and a specified gas such as NOx, CO, or HC are admitted through a given dispersion resistance; (b) a pump cell including an oxygen ion conductive solid electrolyte member, a first pump cell electrode, and a second pump cell electrode which is exposed to the gas cavity, the pump cell being responsive to application of a voltage across the first and second pump cell electrodes to selectively pump oxygen molecules into and out of the gas cavity for adjusting a concentration of the oxygen molecules within the gas cavity to a desired value; (c) a sensor cell including an oxygen ion conductive solid electrolyte member, a first sensor cell electrode, and a second sensor cell electrode which is exposed to the gas cavity, the sensor cell being supplied with electric power through the first and second sensor cell electrodes to produce an electric current as a function of a concentration of the specified gas within the gas cavity; (d) a monitor cell including an oxygen ion-conducting member, a first monitor cell electrode, and a second monitor cell electrode which is exposed to the gas cavity, the oxygen monitor cell being supplied with electric power through the first and second monitor cell electrodes to produce an electric current as a function of a concentration of the oxygen molecules within the gas cavity; (e) a sensor cell power supply working to supply the electric power to the sensor cell; (f) a monitor cell power supply working to supply the electric power to the monitor cell; (g) a sensor cell current detector measuring the current produced by the sensor cell; and (h) a monitor cell current detector measuring the current produced by the monitor cell. The sensor cell current detector is disposed between the second sensor cell electrode exposed to the gas cavity and the sensor cell power supply. Similarly, the monitor cell current detector is disposed between the second monitor cell electrode exposed to the gas cavity and the monitor cell power supply. This enables the sensor cell current and the monitor cell current to be measured without addition of electric noises arising from current components flowing from the monitor cell to the sensor cell and vice versa.

In the preferred mode of the invention, the gas sensor further comprises a control circuit which works to control the voltage applied to the pump cell so as to bring the current measured by the monitor cell current detector into agreement with a constant value.

The gas sensor may also include a concentration measuring circuit working to determine a difference between the currents measured by the monitor cell current detector and the sensor cell current detector to provide a signal indicative of the concentration of the specified gas within the gas cavity.

The oxygen ion conductive solid electrolyte members of the sensor cell and the monitor cell may be formed by a one-piece member.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1A:
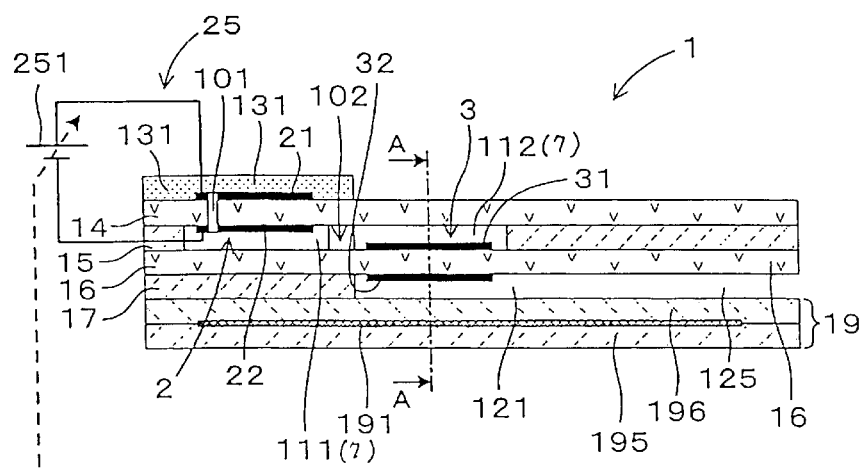
FIG. 1(a) is a longitudinal sectional view which shows a gas sensor according to the first embodiment of the invention.
Figure 1B:
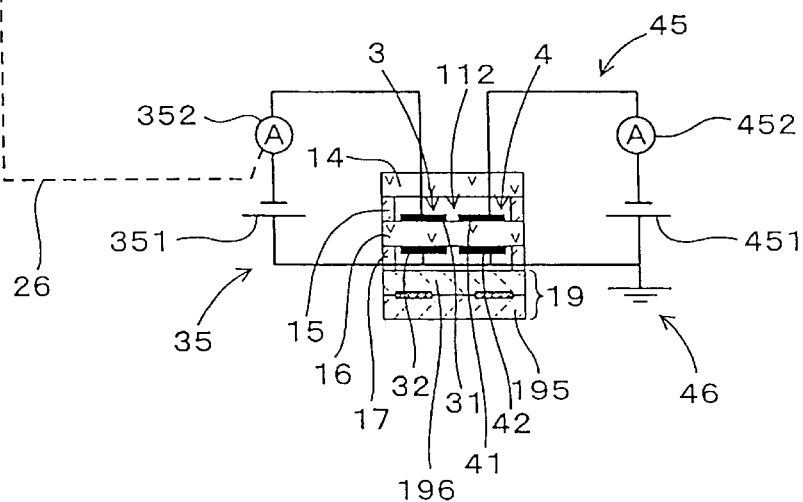
FIG. 1(b) is a transverse sectional view taken along the line A—A in FIG. 1(a)

Referring now to the drawings, wherein like numbers refer to like parts in several views, particularly to FIGS. 1(a) and 1(b), there is shown a gas sensor 1 according to the invention which may be installed in an exhaust pipe of an internal combustion engine to measure the concentration of an oxygen-containing gas component which is dissociative to produce oxygen ions or an oxygen-active gas component which is reactive to oxygen ions such as NOx, CO, or HC contained in exhaust gasses for use in engine burning control and/or catalytic systems.

The following discussion will refer, as an example, to such measurement of NOx contained in exhaust gasses of an automotive engines. For the measurement of the NOx concentration in the exhaust gasses, the gas sensor 1 is disposed within a cylindrical casing and installed in the exhaust pipe with a left end thereof, as viewed in the drawing, exposed to the exhaust gasses and a right end thereof exposed to air used as a reference gas.

The gas sensor element 1 includes generally a first oxygen ion conductive solid electrolyte plate 14, a second oxygen ion conductive solid electrolyte plate 16, a pump cell 2, a monitor cell 3, and a sensor cell 4.

The first solid electrolyte plate 14 forms the oxygen pump cell 2 together with electrodes 21 and 22 disposed on opposed surfaces of the first solid electrolyte plate 14. The second solid electrolyte plate 16 forms the monitor cell 3 together with a measurement gas electrode 31 and a reference electrode 32 and the sensor cell 4 together with a measurement gas electrode 41 and a reference electrode 42.

The gas sensor 1 also includes a pump circuit 25, a monitor circuit 35, and a sensor circuit 45. The pump circuit 25 has a pump cell power supply 251 and is connected to the electrodes 21 and 22 of the pump cell 2. The monitor circuit 35 has a monitor cell power supply 351 and is connected to the electrodes 31 and 32 of the monitor cell 3. The sensor circuit 45 has a sensor cell power supply 451 and is connected to the electrodes 41 and 42 of the sensor cell 4. The monitor circuit 35 also has a monitor cell current detector 352 which measures the current flowing through the electrodes 31 and 32 of the monitor cell 3. The sensor circuit 45 also has a sensor cell current detector 452 which measures the current flowing through the electrodes 41 and 42 of the sensor cell 4.

The gas sensor 1 also includes a first spacer 15, a second spacer 17, and a heater 19 which are laminated together with the first and second solid electrolyte plates 14 and 16. The first spacer 15 defines a gas cavity 7 between the first and second solid electrolyte plates 14 and 16 to which exhaust gasses are introduced. The second spacer 17 defines a reference gas cavity 121 between the second solid electrolyte plate 16 and the heater 19. The heater 16 works to heat up the pump cell 2, the monitor cell 3, and the sensor cell 4 a desired activation temperature.

Figure 2:
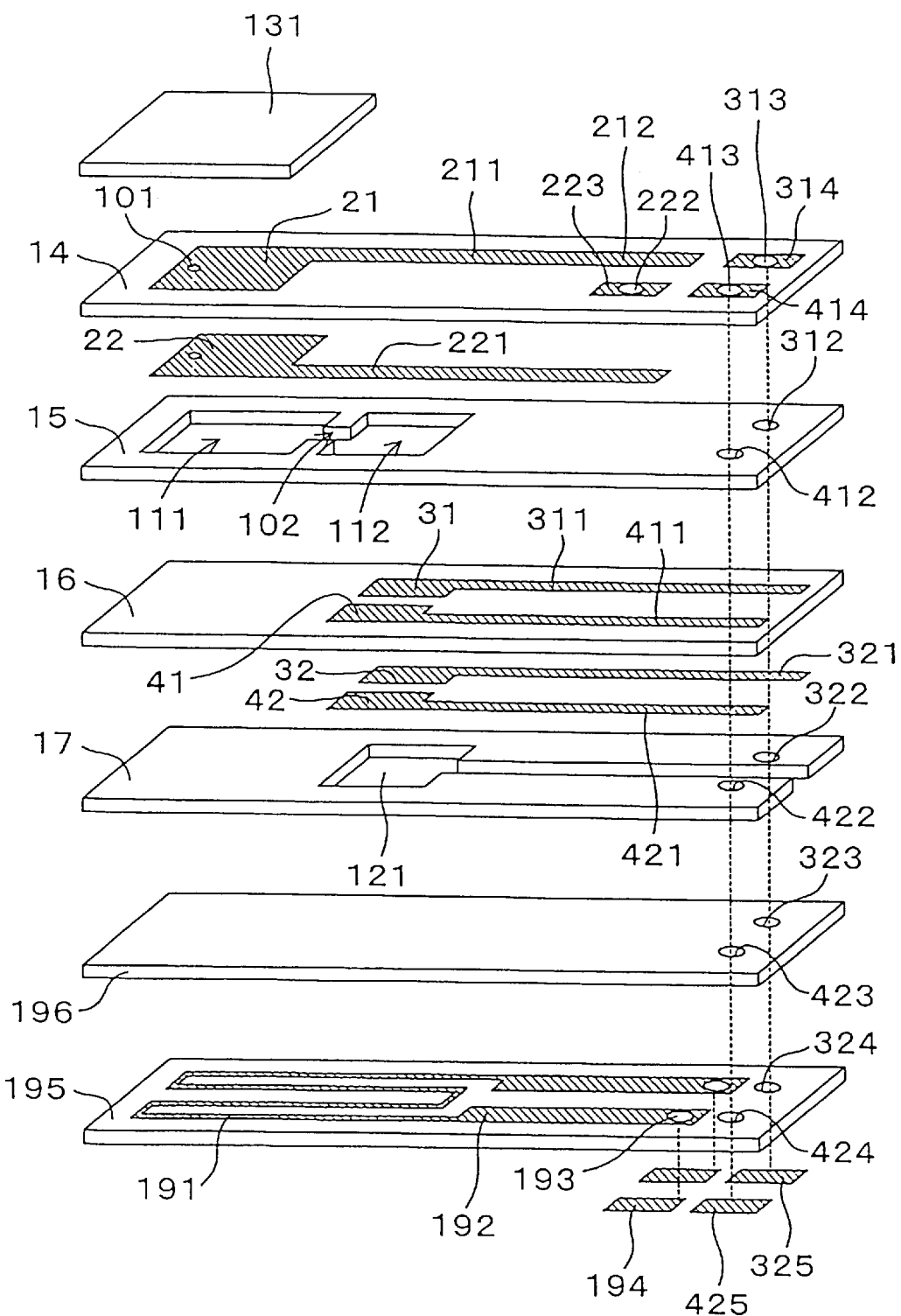
FIG. 2 is an exploded perspective view which shows a sensor element of the gas sensor of FIGS. 1(a) and 1(b)

The gas cavity 7 is, as clearly shown in FIG. 2, made up of a first measurement gas chamber 111 and a second measurement gas chamber 112 defined by windows formed in the spacer 15. The first and second measurement gas chambers 111 and 112 lead to each other through an orifice 102 and arrayed in a lengthwise direction of the gas sensor 1 (i.e., the direction of flow of the gasses). The orifice 102 works as a diffusion resistor.

The first measurement gas chamber 111 leads inside the exhaust pipe through a pinhole (i.e., a gas inlet hole) 101 which is formed through a thickness of a tip of the first solid electrolyte plate 14 and serves as a diffusion resistor. The size of the pinhole 101 is so selected as to bring a diffusion rate of the measurement gas admitted therethrough into the first and second measurement gas chambers 111 and 112 into agreement with a desired one.

The first solid electrolyte plate 14 has disposed thereon a porous protective layer 131 made of a porous alumina material, for example. The protective layer 131 covers the electrode 21 of the pump cell 2 and the pinhole 101 for protecting each electrode exposed to the first and second gas measurement chambers 111 and 112 from harmful gaseous components and preventing the pinhole 101 from clogging. Instead of the pinhole 101, a measurement gas permeable porous member may be disposed in the tip of the first solid electrolyte plate 14.

The reference gas cavity 121 leads outside the exhaust pipe or to the ambient atmosphere for admitting thereinto the air used as a reference gas which is constant in oxygen concentration. The reference gas cavity 121 is, as clearly shown in FIG. 2, defined by a square window formed in the second spacer 17. The reference gas cavity 121 leads to the atmosphere through a slit extending in the lengthwise direction of the second spacer 17. The first and second spacers 15 and 17 are made of an insulating material such as alumina. The first and second solid electrolyte plates 14 and 16 are each made of an oxygen ion conductive electrolyte such as zirconia or ceria.

The pump cell 2, as described above, has the electrodes 21 and 22. The electrode 22 is exposed to the first measurement gas chamber 111 located upstream of the second measurement gas chamber 112 in the flow of the gasses. The electrode 21 is laid on the outside surface of the first solid electrolyte plate 14 and covered with the protective layer 131. The pump cell 2 works to reduce and dissociate or ionize oxygen molecules ($O_2$) contained the exhaust gasses existing outside the gas sensor 1 and pump them into the gas cavity 7 and also to dissociate or ionize and pump the oxygen molecules ($O_2$) outside the gas cavity 7 when the concentration of oxygen within the gas cavity 7 is higher than a given level for keeping the concentration of oxygen molecules within the gas cavity 7 at the given level.

The sensor cell 4, as described above, has the reference electrode 42 and the measurement gas electrode 41 laid on the opposed surfaces of the second solid electrolyte plate 16. The measurement gas electrode 41 is exposed to the second measurement gas chamber 112. The reference electrode 42 is exposed to the reference gas cavity 121. The sensor cell 4 works to discharge oxygen produced when NOx molecules contained in the exhaust gasses are dissociated within the second measurement gas chamber 112 to the reference gas cavity 121 to measure the concentration of NOx molecules.

The monitor cell 3, like the sensor cell 4, has the reference electrode 32 and the measurement gas electrode 31 disposed on the opposed surfaces of the second solid electrolyte plate 16. The reference electrode 32 is exposed to the reference gas cavity 121. The measurement gas electrode 31 is exposed to the second measurement gas chamber 112. The monitor cell 3 works to measure the concentration of oxygen molecules within the second measurement gas chamber 112.

The electrode 22 of the pump cell 2 exposed to the first measurement gas chamber 111 and the electrode 31 of the monitor cell 3 exposed to the second measurement gas chamber 112 are preferably made of a material which is inactive with respect to NOx or hardly dissociate NOx for minimizing a dissociated amount of NOx contained in the gasses. For instance, porous cermet electrodes containing main components of Pt and Au may be used. A metal component of the cermet electrodes preferably contains 1% to 10% by weight of Au. If the Au content is more than 10%, it may result in an excessive reduction in activation of the electrodes. Alternatively, if less than 1%, it may result in an undesirable increase in activation of the electrodes.

The electrode 41 of the sensor cell 4 exposed to the second measurement gas chamber 112 is preferably made of a material which is highly active to NOx or capable of dissociating NOx easily. For instance, a porous cermet electrode which contains Pt and Rh may be used. A metal component of the cermet electrode preferably contains 10% to 50% by weight of Rh. If the Rh content is more than 50%, it may result in instability of performance of the electrodes because of oxygen occlusion of Rh. Alternatively, if the Rh content is less than 10%, it may result in an undesirable reduction in oxygen dissociating activity of the electrodes.

The electrode 21 of the pump cell 2, the electrode 32 of the monitor cell 3, and the electrode 42 of the sensor cell 4 are preferably implemented by porous cermet electrodes containing Pt.

The electrodes 21 and 22 of the pump cell 2, the electrodes 31 and 32 of the monitor cell 3, and the electrodes 41 and 42 of the sensor cell 4, as clearly shown in FIG. 2, have leads 211, 221, 311, 321, 411, and 421 extending on one of the first and second solid electrolyte plates 14 and 16.

The leads 211, 221, 311, 321, 411, and 421 communicate with terminals 212, 223, 314, 325, 414, and 425 through holes 222, 312, 313, 322, 323, 324, 412, 413, 422, 423, and 424. The terminals 212 and 223 are electrically connected to the pump circuit 25. The terminals 314 and 325 are electrically connected to the monitor circuit 35. Similarly, the terminals 414 and 425 are electrically connected to the sensor circuit 45. The reference electrodes 32 and 42 are, as clearly shown in FIG. 1(b), connected to a grounding terminal 46. The monitor circuit 35 connects with the pump cell power supply 251 of the pump circuit 25 through a feedback circuit 26.

It is advisable that insulating layers made of, for example, alumina be formed on areas of the opposed major surfaces of the first and second solid electrolyte plates 14 and 16 other than areas on which the electrodes 21, 22, 31, 32, 41, and 42 are formed, especially between the leads 221, 211, 311, 321, 411, and 421 and the surfaces of the first and second solid electrolyte plates 14 and 16.

The heater 16 is made of a lamination of a heater sheet 195 and an insulating layer 196 made of alumina. The heater sheet 195 is made of an insulating material such as alumina and has patterned thereon a heater electrode 191 which is electrically connected to a terminal 194 through a lead 192 and a hole 193. The electric power is supplied to the heater electrode 191 through the terminal 194 to heat the cells 2, 3, and 4 up to a given activating temperature. The heater electrode 191 may be implemented by a cermet electrode made of Pt and ceramic such as alumina.

The formation of the gas sensor 1 may be accomplished by making sheets for the solid electrolyte plates 14 and 15 and the spacers 15 and 17 using extrusion molding techniques, forming all the electrodes on the sheets by screen printing, laying the sheets to overlap each other, and firing them.

The operation of the gas sensor 1 will be described below in brief.

The exhaust gasses containing $O_2$, NOx, $H_2O$, etc. are admitted into the first measurement gas chamber 111 of the gas cavity 7 through the porous protective layer 131 and the pinhole 101. The amount of the exhaust gasses entering the gas cavity 7 depends upon the diffusion resistances of the porous protective layer 131 and the pinhole 101. The exhaust gasses pass through the orifice 102 and reach the second measurement gas chamber 112.

Application of voltage across the electrodes 21 and 22 of the pump cell 2 through the pump cell power supply 251 of the pump circuit 25 so that a positive potential may be developed at the electrode 21 will cause oxygen molecules within the first measurement gas chamber 111 to be ionized on the electrode 22 and pumped or transferred to the electrode 21. Conversely, application of voltage across the electrodes 21 and 22 of the pump cell 2 so that a positive potential may be developed at the electrode 22 will cause oxygen molecules and water vapor within the exhaust pipe of the engine to be ionized on the electrode 21 and pumped or transferred to the electrode 22. With such oxygen pumping, the concentration of oxygen molecules within the gas cavity 7 is controlled by changing the magnitude and orientation of the voltage applied across the electrodes 21 and 22 of the pump cell 2.

The voltage (e.g., 0.40V) is applied across the electrodes 31 and 32 of the monitor cell 3 so that a positive potential may be developed at the electrode 32 exposed to the reference gas cavity 121. This will cause oxygen molecules within the second measurement gas chamber 112 to be ionized on the electrode 31 and pumped or transferred to the electrode 32. The electrode 31 is, as described above, a Pt—Au cermet electrode inactive with NOx that is a target gas component to be measured, therefore, an oxygen ion current (will also be called a monitor cell current below) flows between the electrodes 31 and 32 as a function of the amount of $O_2$ passing through the porous protective layer 131 and the pinhole 101 and entering the first measurement gas chamber 111 and the second measurement gas chamber 112 regardless of the amount of NOx. The concentration of oxygen molecules within the gas cavity 7 is kept constant by measuring the monitor cell current flowing between the electrodes 31 and 32 through the monitor cell current detector 352, as shown in FIG. 1(b), and controlling the voltage applied to the electrodes 21 and 22 of the pump cell 2 through the feedback circuit 26 so as to keep the monitor cell current at a constant value (e.g., 0.5 $\mu$A).

The voltage (e.g., 0.04V) is applied across the electrodes 41 and 42 of the sensor cell 4 so that a positive potential may be developed at the electrode 42 exposed to the reference gas cavity 121. This will cause oxygen molecules and NOx molecules within the second measurement gas chamber 112 of the gas cavity 7 to be ionized on the electrode 41, so that oxygen ions are pumped or transferred to the electrode 42 because the electrode 41 is, as described above, implemented by the Pt—Rh cermet electrode which is active with NOx. An oxygen ion current (will also called a sensor cell current below), thus, flows through the electrodes 41 and 42 as a function of the concentration of NOx in the second measurement gas chamber 112.

Therefore, controlling the voltage applied to the pump cell 2 so as to keep the monitor cell current flowing through the monitor cell 3 at a constant level (e.g., 0.5 $\mu$A) causes the sensor cell current flowing between the electrodes 41 and 42 of the sensor cell 4 to be kept at a constant level (e.g., 0.5 $\mu$A) if the gasses contain no NOx. Alternatively, if the gasses contain NOx molecules, it will cause the quantity of oxygen ions produced by the dissociation of the NOx molecules to increase, thus causing the sensor cell current flowing through the sensor cell 4 to increase as a function of the concentration of NOx. The concentration of NOx contained in the gasses may, thus, be determined with a higher degree of accuracy regardless of oxygen molecules contained in the gasses by measuring the sensor cell current flowing between the electrodes 41 and 42 of the sensor cell 4 using the sensor cell current detector 452.

Figure 3:
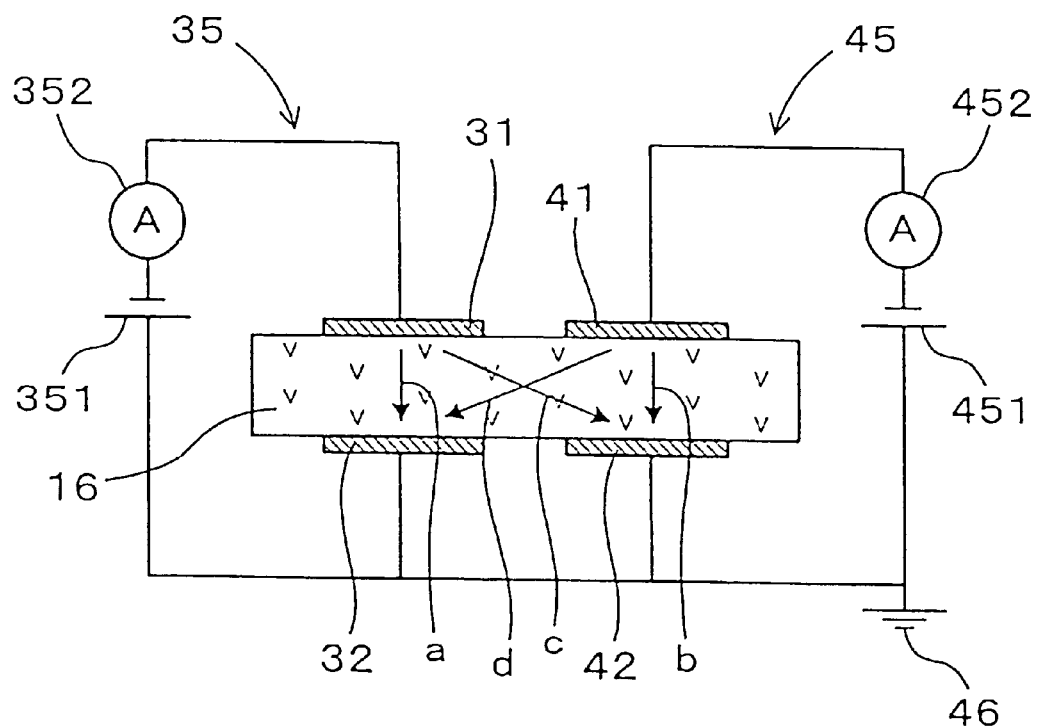
FIG. 3 is a transverse sectional view which shows electric connections between sensor and monitor cells and current detectors thereof.
Figure 7:
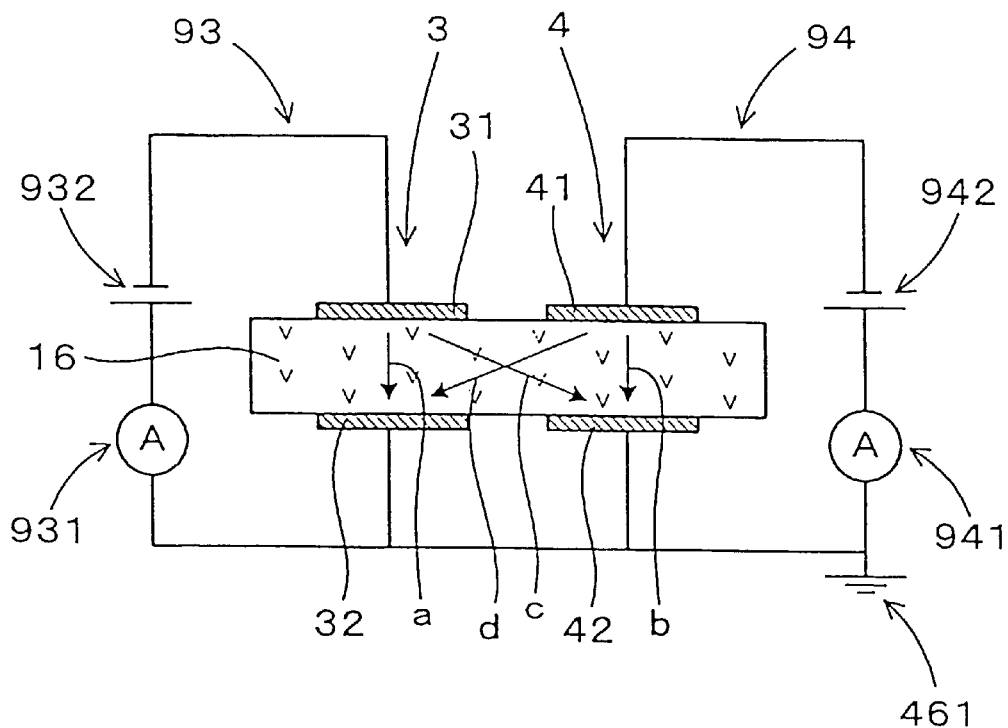
FIG. 7 is a transverse sectional view which shows electric connections between sensor and monitor cells and current detectors thereof in a comparative structure of a gas sensor.

The monitor cell current produced by the monitor cell 3 flows, as indicated by arrows a and c in FIG. 3, from the electrode 31 both to the electrode 32 and to the adjacent electrode 42 of the sensor cell 4. Similarly, the sensor cell current produced by the sensor cell 4 flows, as indicated by arrows b and d in FIG. 3, from the electrode 41 both to the electrode 42 and to the adjacent electrode 32 of the monitor cell 3. In the case, as illustrated in FIG. 7, where the monitor cell current detector 931 and the sensor cell current detector 941 are installed between the monitor cell power supply 932 and the electrode 32 of the monitor cell 3 and between the sensor cell power supply 942 and the electrode 42 of the sensor cell 4, respectively, the monitor cell current detector 931 picks up the current component a of the monitor cell current and the current component d of the sensor cell current, and the sensor cell current detector 941 picks up the current component b of the sensor cell current and the current component c of the monitor cell current, thus resulting errors in determining the concentrations of oxygen and NOx.

In order to avoid the above problem, the structure of this embodiment, as clearly shown in FIG. 3, has the monitor cell current detector 352 and the sensor cell current detector 452 disposed on the positive sides of the monitor cell power supply 351 and the sensor cell power supply 451, that is, between the monitor cell power supply 351 and the electrode 31 of the monitor cell 3 and between the sensor cell power supply 451 and the electrode 41 of the sensor cell 4, respectively. The monitor cell current detector 352, thus, measures both the current components a and c of the monitor cell current, while the sensor cell current detector 452 measures both the current components b and d of the sensor cell current, thereby enabling the concentrations of oxygen and NOx to be determined correctly.

Figures 4A, 4B:
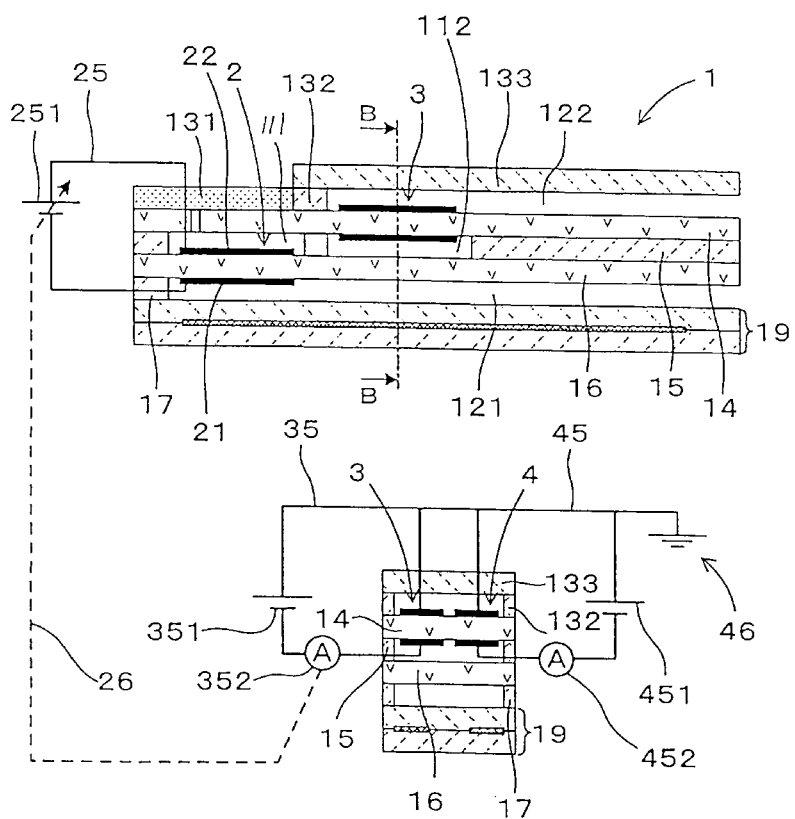
FIG. 4(a) is a longitudinal sectional view which shows a gas sensor according to the second embodiment of the invention.
FIG. 4(b) is a transverse sectional view taken along the line B—B in FIG. 4(a)

FIGS. 4(a) and 4(b) illustrate the gas sensor 1 according to the second embodiment of the invention.

The gas sensor 1 has a second reference gas cavity 122 leading to the ambient atmosphere. The monitor cell 3 and the sensor cell 4 are, as can be seen from FIG. 4(b), exposed to the second measurement gas chamber 112 and the second reference gas cavity 122. The pump cell 2 is exposed to the first measurement gas chamber 111 and the first reference gas cavity 121.

The second reference gas cavity 122 is defined by spacers 132 and 133 disposed on the first solid electrolyte plate 14. The spacers 132 and 133 are both made of alumina. Other arrangements and operation are the same as those in the first embodiment, and explanation thereof in detail will be omitted here.

The electrode 21 of the pump cell 2 faces the first reference gas cavity 121, thus enabling the pump cell 2 to pump oxygen molecules out of the ambient atmosphere (i.e., the first reference gas cavity 121) into the first measurement gas chamber 111. This structure, thus, suitable for a case where the exhaust gasses hardly contains an oxygen source such as water vapor.

Figures 5A, 5B:
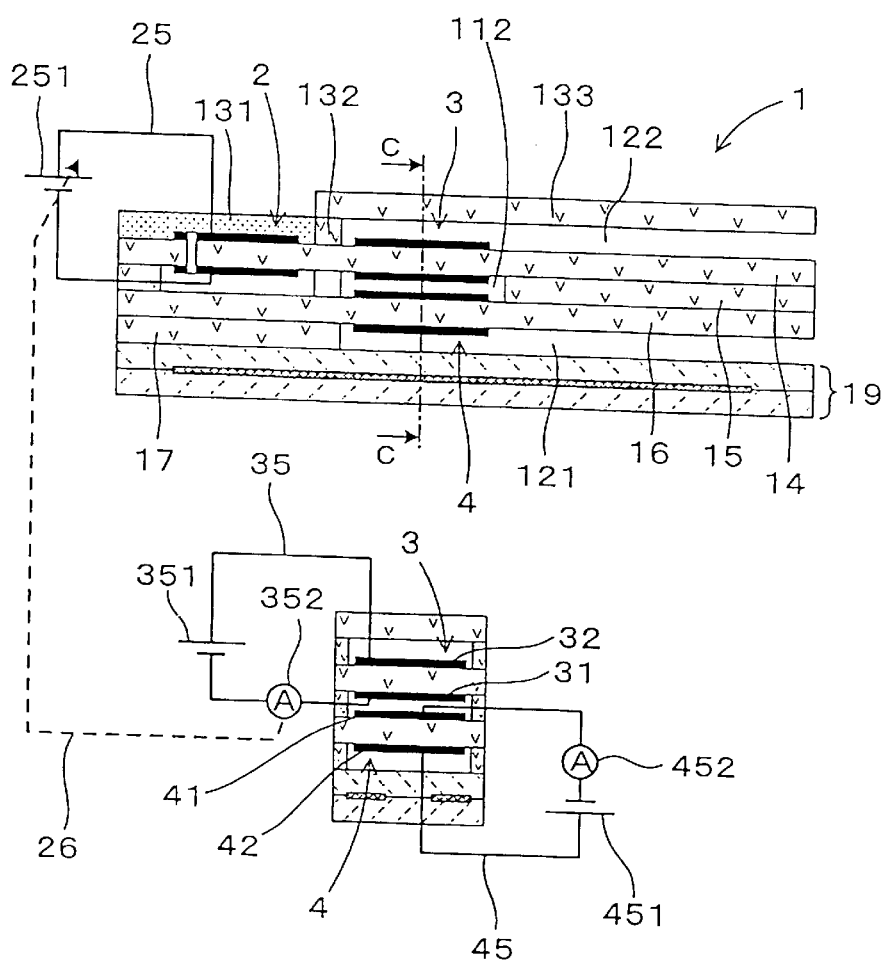
FIG. 5(a) is a longitudinal sectional view which shows a gas sensor according to the third embodiment of the invention.
FIG. 5(b) is a transverse sectional view taken along the line C—C in FIG. 5(a)

FIGS. 5(a) and 5(b) illustrate the gas sensor 1 according to the third embodiment of the invention.

The monitor cell 3 is exposed to the second reference gas cavity 122 and the second measurement gas chamber 112. The sensor cell 4 is disposed between the second measurement gas chamber 112 and the first reference gas cavity 121. The spacers 15, 17, 132, and 133 are made of solid electrolyte plates. Other arrangements are identical with those of the first embodiment, and explanation thereof in detail will be omitted here.

The structure of this embodiment allows the electrodes 31 and 32 of the monitor cell 3 and the electrodes 41 and 42 of the sensor cell 4 to be increased in area as compared with the above embodiments, thereby resulting in a decrease in impedance of the monitor cell 3 and the sensor cell 4. Most of the parts of the gas sensor 1 other than the heater 19 are made of solid electrolyte material, thus resulting in a decrease in joint between different material-made parts, which facilitates ease of manufacturing of the gas sensor 1.

Figure 6A:
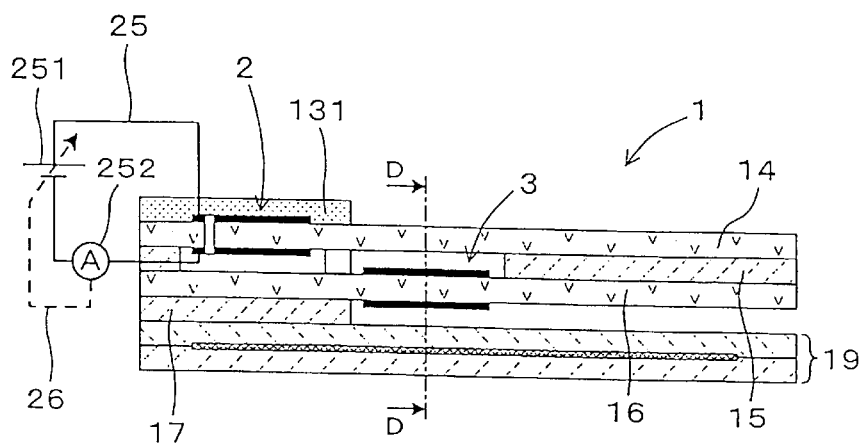
FIG. 6(a) is a longitudinal sectional view which shows a gas sensor according to the fourth embodiment of the invention.
Figure 6B:
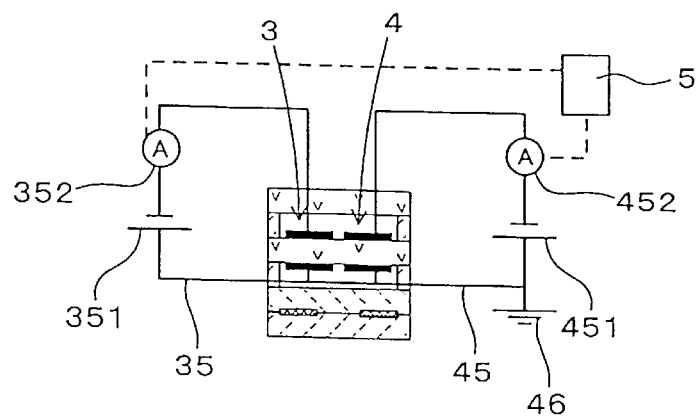
FIG. 6(b) is a transverse sectional view taken along the line D—D in FIG. 6(a)

FIGS. 6(a) and 6(b) illustrates the gas sensor 1 according to the fourth embodiment of the invention which is different from the first embodiment only in structure of the pump circuit 25, the monitor circuit 35, and the sensor circuit 45.

The pump circuit 25 includes the pump cell power supply 251 and the pump cell current detector 252. The pump cell current detector 252 measures the pump cell current flowing through the pump cell 2. The feedback circuit 26 monitors an output of the pump cell current detector 252 and adjusts the voltage applied to the pump cell 2 through the pump cell power supply 251 to a level which meets a preselected pump current-to-pump cell applied voltage relattion.

The monitor cell current detector 352 and the sensor cell current detector 452 are connected to a current difference detector 5. The current difference detector 5 determines a difference in output between the monitor current detector 352 and the sensor current detector 452 and provides a signal indicative of the concentration of NOx. The monitor cell current is a function of the concentration of oxygen within the second measurement gas chamber 112. The sensor cell current is a function of the sum of the concentrations of oxygen and NOx within the second measurement gas chamber 112. The current difference, as determined by the current difference detector 5, therefore, represents the concentration of NOx within the second measurement gas chamber 112.

Other arrangements are identical with those in the first embodiment, and explanation thereof in detail will be omitted here.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas sensor comprising:

a gas cavity into which gasses consisting essentially of oxygen molecules and a specified gas are admitted through a given dispersion resistance;

a pump cell including an oxygen ion conductive solid electrolyte member, a first pump cell electrode, and a second pump cell electrode which is exposed to the gas cavity, said pump cell being responsive to application of a voltage across the first and second pump cell electrodes to selectively pump oxygen molecules into and out of said gas cavity for adjusting a concentration of the oxygen molecules within said gas cavity to a desired value;

a sensor cell including an oxygen ion conductive solid electrolyte member, a first sensor cell electrode, and a second sensor cell electrode which is exposed to said gas cavity, said sensor cell being supplied with electric power through the first and second sensor cell electrodes to produce an electric current as a function of a concentration of the specified gas within said gas cavity;

a monitor cell including an oxygen ion-conducting member, a first monitor cell electrode, and a second monitor cell electrode which is exposed to said gas cavity, said oxygen monitor cell being supplied with electric power through the first and second monitor cell electrodes to produce an electric current as a function of a concentration of the oxygen molecules within said gas cavity;

a sensor cell power supply working to supply the electric power to said sensor cell;

a monitor cell power supply working to supply the electric power to said monitor cell;

a sensor cell current detector measuring the current produced by said sensor cell, said sensor cell current detector being disposed between the second sensor cell electrode exposed to said gas cavity and said sensor cell power supply;

a monitor cell current detector measuring the current produced by said monitor cell, said monitor cell current detector being disposed between the second monitor cell electrode exposed to said gas cavity and said monitor cell power supply; and a concentration measuring circuit working to determine a difference between the currents measured by said monitor cell current detector and said sensor cell current detector to provide a signal indicative of the concentration of the specified gas within said gas cavity.

2. A gas sensor as set forth in claim 1, further comprising a control circuit working to control the voltage applied to said pump cell so as to bring the current measured by said monitor cell current detector into agreement with a constant value.

3. A gas sensor as set forth in claim 1, wherein the oxygen ion conductive solid electrolyte members of said sensor cell and the monitor cell are formed by a one-piece member.

4. A gas sensor as set forth in claim 1, wherein the specified gas is one of an oxygen-containing gas which is dissociative to produce oxygen ions and an oxygen-active gas which is reactive to oxygen ions.

* * * * *